United States Patent
Lindmuller et al.

(10) Patent No.: US 9,322,770 B2
(45) Date of Patent: Apr. 26, 2016

(54) METHOD AND CALIBRATION INSERT FOR ADJUSTING, CALIBRATING AND/OR CHECKING A FUNCTION OF A PHOTOMETRIC SENSOR

(71) Applicant: Endress + Hauser Conducta Gesellschaft für Mess—und Regeltechnik mbH + Co. KG, Gerlingen (DE)

(72) Inventors: Peter Lindmuller, Essingen (DE); Matthias Grossmann, Vaihingen-Enz (DE); Thilo Kratschmer, Gerlingen (DE)

(73) Assignee: ENDRESS + HAUSER CONDUCTA GESELLSCHAFT FUR MESS- UND REGELTECHNIK MBH + CO. KG, Gerlingen (DE)

( * ) Notice: Subject to any disclaimer, the term of this patent is extended or adjusted under 35 U.S.C. 154(b) by 0 days.

(21) Appl. No.: 14/294,210

(22) Filed: Jun. 3, 2014

(65) Prior Publication Data

US 2014/0362381 A1    Dec. 11, 2014

(30) Foreign Application Priority Data

Jun. 6, 2013   (DE) .......................... 10 2013 105 850

(51) Int. Cl.
G01N 21/00 (2006.01)
G01N 21/27 (2006.01)
G01N 21/85 (2006.01)

(52) U.S. Cl.
CPC .......... *G01N 21/278* (2013.01); *G01N 21/8507* (2013.01); *G01N 2021/8535* (2013.01)

(58) Field of Classification Search
CPC ... G01N 21/274; G01N 21/278; G01N 21/59; G01N 21/276; G01N 21/359; G01N 21/55; G01N 21/552; G01N 2201/062; G01N 2201/12746; G01N 2201/129; G01N 15/0227; G01N 15/05; G01N 15/1012; G01N 15/147
See application file for complete search history.

(56) References Cited

U.S. PATENT DOCUMENTS 4,834,532 A * 5/1989 Yount ............................ 356/41
5,616,823 A * 4/1997 Lattimore ..................... 73/1.03

(Continued)

FOREIGN PATENT DOCUMENTS

DE   102007038752 A1   2/2009
DE   102008010559 B4   9/2009

(Continued)

OTHER PUBLICATIONS

German Search Report, DPMA, Munich, Jul. 24, 2013.

*Primary Examiner* — Michael P Stafira
(74) *Attorney, Agent, or Firm* — Bacon & Thomas, PLLC

(57) ABSTRACT

A method for adjusting, calibrating and/or checking a function of a photometric sensor, which is embodied for measuring at least one measured variable in a medium, wherein the sensor works with at least one measuring wavelength and at least one reference wavelength, comprising the steps as follows: mounting a calibration insert in a receptacle provided therefor at the sensor, adjusting, calibrating and/or performing the function check, and removing the calibration insert, characterized in that the transmittance of light of the measuring wavelength and the transmittance of light of the reference wavelength through the calibration insert are different. The invention relates further to a calibration insert.

8 Claims, 1 Drawing Sheet

(56) References Cited

U.S. PATENT DOCUMENTS

| | | | |
|---|---|---|---|
| 5,705,811 A * | 1/1998 | Harder et al. | 250/232 |
| 5,924,981 A * | 7/1999 | Rothfritz et al. | 600/306 |
| 6,045,502 A * | 4/2000 | Eppstein et al. | 600/306 |
| 2003/0020909 A1 * | 1/2003 | Adams et al. | 356/326 |
| 2008/0309930 A1 * | 12/2008 | Rensen | 356/300 |
| 2009/0094847 A1 * | 4/2009 | Clifford | 33/502 |
| 2011/0023575 A1 * | 2/2011 | Al-Ali | 73/1.03 |
| 2011/0127414 A1 | 6/2011 | Engelhardt | |
| 2011/0211192 A1 * | 9/2011 | Kimura et al. | 356/243.1 |
| 2012/0223220 A1 * | 9/2012 | Arai | 250/252.1 |
| 2013/0223685 A1 * | 8/2013 | Maiden | 382/103 |
| 2014/0300725 A1 * | 10/2014 | Wei et al. | 348/80 |

FOREIGN PATENT DOCUMENTS

| | | |
|---|---|---|
| DE | 102009047303 A1 | 6/2011 |
| DE | 102010060721 B3 | 4/2012 |
| DE | 102011086392 A1 | 5/2013 |
| DE | 102011121195 A1 | 6/2013 |

* cited by examiner

METHOD AND CALIBRATION INSERT FOR ADJUSTING, CALIBRATING AND/OR CHECKING A FUNCTION OF A PHOTOMETRIC SENSOR

TECHNICAL FIELD

The invention relates to a method and a calibration insert for adjusting, calibrating and/or checking a function of a photometric sensor, which is embodied for measuring at least one measured variable in a medium.

BACKGROUND DISCUSSION

In the following, the invention will be described especially on the basis of nitrate sensors and SAC sensors. The invention is, however, not limited thereto, but, instead, relates to photometric sensors in general. Measuring devices suitable for determining the corresponding process variables are manufactured and sold by the group of firms, Endress+Hauser, in a large multiplicity of variants, for example, under the designation "Viomax CAS51D".

The acronym "SAC" stands for spectral absorption coefficient. A "SAC sensor" herein means a sensor, which determines the spectral absorption coefficient by means of absorption of measuring radiation by certain substances of a medium. Especially thereby, the total organic carbon (TOC) contributing to the SAC value and the chemical oxygen demand (COD) can be determined. From the SAC value, the TOC value, respectively the COD value, can be deduced.

In the case of SAC sensors and nitrate sensors, as a rule, the measured value is determined via an absorption measurement at a measuring wavelength and at a reference wavelength. These wavelengths are located in the UV and UV-VIS regions. A possible measuring wavelength and reference wavelength combination for nitrate is 214 nm and 254 nm and for SAC, 254 nm and 550 nm. Other combinations are, however, possible. The measuring principle will be explained briefly based on a nitrate sensor. The section of the sensor immersed in the medium has a gap (the cuvette gap), into which the medium can penetrate. The gap is traversed by a measuring beam (having a measuring wavelength) and a reference beam (having a reference wavelength). Nitrate ions contained in the medium, and therewith in the gap, absorb the light in the region of the measuring wavelength of 214 nm in proportion to their concentration, while the UV light in the reference channel at 254 nm remains almost unchanged. Used as measurement result is the ratio between the reference channel and the measurement channel. This ratio is converted into the nitrate concentration based on a stored calibration curve.

The calibration curve is obtained earlier via suitable calibration means. Frequently, certain standard liquids are used. Typical calibration means for nitrate sensors are solutions of nitrate hydrogen phthalate (NHP) or potassium hydrogen phthalate (KHP). These standard solutions have, however, disadvantages as follows: Limited storability, multiple use doubtful because of possible standard solution contamination, and expensive for the sensor operator. Due to the frequently to be performed calibrations/adjustments and function testings with standards, these sensors represent a significant burden for the sensor operator.

As an alternative to liquid solutions, solid standards are a possibility. Solid standards can be stored longer, provided that materials that age are not used. Additionally, their handling is less of a problem.

German Patent DE 10 2009 028 254 A1 discloses a solid standard, which has in a certain configuration a similar spectral behavior as KHP, and, thus, simulates a certain concentration of KHP. Other concentrations of KHP or other calibration means cannot be simulated by this disclosed solid standard. The standard is additionally fixedly arranged in the device.

A contamination check, and therewith a function review, is implemented, for instance, by one or more control filters installed in the apparatus. These control filters have a defined absorption and weaken the light by a certain amount. Fouling is present when a difference from the expected measured value is detected.

There are systems with a plurality of filters, which are introduced alternately or simultaneously into the optical path, i.e., for example, into the earlier described gap, in order to perform a verification or calibration. U.S. Pat. No. 6,977,365 B1 shows such filters. The filters are, in such case, embodied as differently gray filters, so that, depending on filter set, a weakening can be detected compared with measuring without filtering. One obtains thus a number of (filter-)measured values compared with measuring without filtering, however, without any wavelength dependent information. In this way, indeed, the slope of the calibration curve can be determined and, in given cases, readjusted, but a determining of the y-intercept is not possible.

SUMMARY OF THE INVENTION

An object of the invention is to provide an opportunity for performing for photometric sensors universal and complete calibrations using calibration means stable over long periods of time.

The object is achieved by a method comprising steps as follows: mounting a calibration insert in a receptacle provided therefor at the sensor; adjusting, calibrating and/or performing the function check; and removing the calibration insert. The method is characterized by the feature that the transmittance of light of the measuring wavelength and the transmittance of light of the reference wavelength through the calibration insert are different.

In an advantageous embodiment, the quotient of transmittance of light of the measuring wavelength and transmittance of light of the reference wavelength through the calibration insert is a direct measure for the measured variable, especially in units of the measured variable.

Because the transmittance of measuring and reference wavelengths are different, it is possible using the Lambert-Beer law to calibrate directly in measured value units, e.g. in mass per volume, thus for instance, g/l. The measured values can, in this way, be associated directly with a concentration value. In turn, not only the slope but now the complete characteristics of the calibration curve can be tested, evaluated, calibrated and, in given cases, adjusted. Without interruption of the measuring chain, the total measuring range can be tested and evaluated.

In contrast to the state of the art, any selected calibration insert can be used. For an appropriate calibrating, only a different transmission of the measuring and reference wavelengths is necessary; the calibration insert needs no spectrum similar to that of a liquid standard and can be universally applied.

Preferably, the measure is adjustable, i.e. the calibration insert permits different values to be output directly in the units of measurement. An opportunity, in such case, is the serial arrangement of calibration inserts and/or the application of different calibration inserts. The calibration insert is exchangeable and simply different inserts can be used for different concentrations.

In an advantageous form of embodiment, the transmittance of light of the reference wavelength is greater than the transmittance of light of the measuring wavelength.

In a preferred form of embodiment, the calibration insert is so embodied that it can be placed repeatably equally in the receptacle. In this way, it can be assured that a calibration is always performed under the same conditions.

The object is further achieved by a calibration insert comprising: a housing, wherein the housing is essentially transparent for the measuring wavelength and the reference wavelength; and a solid body, wherein the solid body is located in the housing. The calibration insert is characterized by the feature that the transmittance of light of the measuring wavelength and the transmittance of light of the reference wavelength through the solid body are different.

Preferably, the transmittance of light of the reference wavelength and the transmittance of light of the measuring wavelength are each constant with time and environmental influences. Especially, it is meant that the transmission characteristics remain constant over a plurality of measurements, even under the influence of the measuring and reference wavelengths.

In an embodiment, the solid body is an optical glass, especially quartz glass of "IR grade". Especially, the solid body is a glass of brand name, "Infrasil", "Vitreosil IR", etc. Alternatively, the solid body is an organic material of defined transparency.

Preferably, the calibration insert is so embodied that it can be placed repeatably at the same position at the sensor, wherein the calibration insert prevents that disturbing light, especially ambient light, acts on the solid body, and wherein the calibration insert protects the solid body against contamination.

An advantageous form of embodiment comprises an arrangement comprising a sensor and an above described calibration insert.

Preferably, the calibration insert is, in such case, so positioned at the sensor that the sensor is calibrated, adjusted and/or subjected to a function check.

In an embodiment, the sensor is a nitrate sensor or a SAC sensor.

BRIEF DESCRIPTION OF THE DRAWINGS

The invention will now be explained in greater detail based on the drawing, the figures of which show as follows.

DETAILED DISCUSSION IN CONJUNCTION WITH THE DRAWINGS

Figure 1:
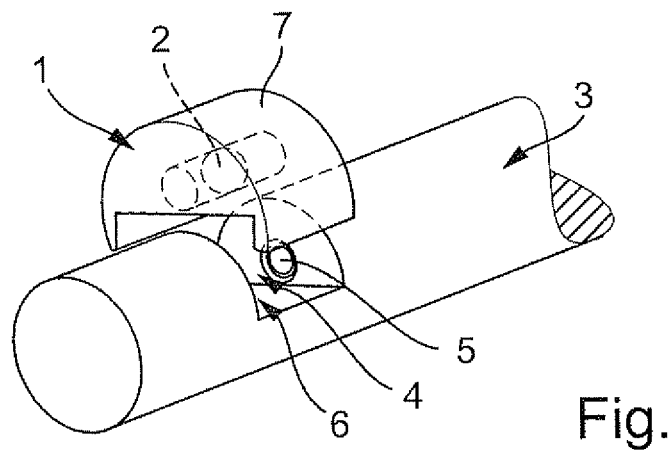
FIG. 1 is a calibration insert of the invention before mounting on a sensor.

In the figures, equal features are provided with equal reference characters.

FIG. 1 shows a photometric sensor 3, for instance, a nitrate sensor or SAC sensor. Sensor 3 is immersed in the medium to be measured (not shown). Especially, the gap 4 is covered by medium.

Light from an emitter 5 passes through the gap 4. Emitter 5 can be, for instance, a pulsed flash lamp or a number of LEDs. The flash lamp emits a spectrum, which contains at least light of a measuring wavelength and light of a reference wavelength. The LEDs are embodied for emitting light of the appropriate measuring wavelength and reference wavelength. Selected for the wavelengths can be, for example, in the case of nitrate, 214 nm and 254 nm, and in the case of SAC, 254 nm and 550 nm.

Located on the oppositely lying side is a receiver 6. Receiver 6 is embodied, for instance, as a receiver arrangement. The receiver arrangement includes, for example, a beam divider, which leads the light from the emitter 5 to a measurement receiver for receiving light of the measuring wavelength and to a reference receiver for receiving light of the reference wavelength. Placed in front of the two receivers is, in each case, a filter, which in the case of the measurement receiver passes only light of the measuring wavelength and in the case of the reference receiver only light of the reference wavelength. The receivers are photodiodes, for instance.

Between receiver 6, respectively emitter 5, and gap 4 (thus medium) for protective purposes are windows, which are transparent for the measuring and reference wavelengths. Depending on need, other optical systems, such as lenses, etc., can be provided for better beam guidance.

In the gap 4, the substances to be measured, thus, for instance, nitrate ions, absorb the light in the region of the measuring wavelength (214 nm) in proportion to their concentration, while the light in the reference channel (254 nm) remains almost unchanged. Disturbing influences from e.g. turbidity, fouling or organic hydrocarbons are eliminated mathematically. Used as measurement result is the signal ratio between the reference channel and the measurement channel. The measuring principle is based on the Lambert-Beer law, where, in its valid region, there is a linear dependence between the absorption of light and the concentration of the absorbing substance.

Besides the sensor 3, FIG. 1 shows a calibration insert 1 of the invention. Calibration insert 1 includes a housing 7 and a solid body 2. Housing 7 is essentially transparent both for the measuring wavelength as well as also for the reference wavelength. Housing 7 is manufactured, for instance, of a synthetic material, e.g. a plastic.

Figure 2:
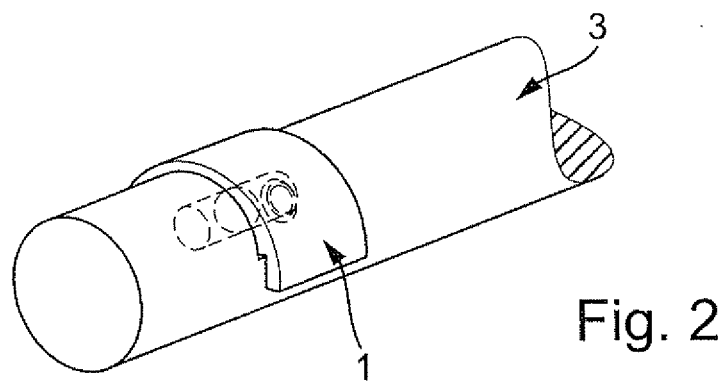
FIG. 2 is a calibration insert of the invention mounted on a sensor.

Located in housing 7 is a solid body 2. In such case, housing 7 is embodied such that it prevents disturbing light, for instance, from the environment, from acting on the solid body, in order that the measuring not be disturbed. Furthermore, the calibration insert protects the solid body from contaminants. Housing 7 is so formed that it fits exactly into the gap 4 of the sensor 3, in order that the calibration insert 1 can, thus, be repeatably placed at the same position on the sensor 3. FIG. 2 shows this position, in which the calibration insert 1 is located in the gap 4 at the sensor 3. Sensor 3 is thus embodied in the region of the gap 4 to provide a receptacle, or seat, for the calibration insert 1.

For calibrating, for checking a function of the sensor 3 and possibly for adjusting, the solid body 2 is so embodied that the transmittance of light of the measuring wavelength and the transmittance of light of the reference wavelength through the solid body are different.

Materials suited therefor include, for instance, certain glasses, such as, for instance, quartz glass of "IR grade" (brand names "Infrasil", "Vitreosil IR", . . . ) or an organic material of defined transparency.

If materials with different transmittances for the measuring and reference wavelengths are used, besides the slope of the calibration curve, also the y-intercept, thus the calibration curve characteristic, can be ascertained. Because of the linear dependence of the Lambert-Beer law in its valid region, these two measured values are sufficient. It is, thus, possible to calibrate directly in units of the measured variable (e.g. nitrate), thus, for instance, in g/l, i.e. mass per unit volume. It is, thus, possible, without interruption of the measuring chain, to test and evaluate the entire measuring range.

The solid body 2 has an absorption at the corresponding wavelengths. The absorption must be neither too high (no light reaches the receiver 6), nor too small (light weakening not measurable). The absorption is, in such case, constant over a plurality of measurements, also under influence of the measuring and reference wavelengths.

The absorption at the measuring wavelength is preferably greater than the absorption at the reference wavelength. The measured ratio of the absorptions at the measuring and reference wavelengths can be associated with a corresponding value of the measured variable (thus, for instance, a nitrate concentration).

Sensor 3 and calibration insert 1 are embodied as two different systems. It is then possible to produce different calibration inserts 1 for different fields of application. A typical case of application would be a calibration insert 1 for a low concentration, e.g. 0.1 mg/l, and one or more calibration inserts 1 for middle, e.g. 5 mg/l, respectively higher concentrations, e.g. 100 mg/l. A higher concentration can be achieved by arranging a plurality of solid bodies 2 one after the other or by using a greater thickness of the solid body 2. Also, another material with a smaller transmittance can be selected.

The invention claimed is:

1. A calibration insert for adjusting, calibrating and/or checking a function of a nitrate or SAC sensor, which is embodied for measuring at least one measured variable in a medium, said sensor works with at least one measuring wavelength and at least one reference wavelength, wherein the measuring wavelength and the reference wavelength are different, the calibration insert comprising:
    a housing, wherein said housing is essentially transparent for the measuring wavelength and for the reference wavelength; and
    a solid body, wherein:
    said solid body is located in said housing; and
    the transmittance of light of the measuring wavelength and the transmittance of light of the reference wavelength through said solid body are different.

2. The calibration insert as claimed in claim 1, wherein:
    the quotient of transmittance of light of the measuring wavelength and transmittance of light of the reference wavelength through said calibration insert is a direct measure for the measured variable, especially in units of the measured variable.

3. The calibration insert as claimed in claim 2, wherein the measure for the measured variable is adjustable by at least one of the following:
    serial arrangement of solid bodies,
    variation of thickness of said solid body, and/or
    variation of material of said solid body.

4. The calibration insert as claimed in claim 1, wherein:
    the transmittance of light of the reference wavelength and the transmittance of light of the measuring wavelength are each constant with time and environmental influences.

5. The calibration insert as claimed in claim 1, wherein:
    said solid body is an optical glass, especially quartz glass of "IR grade".

6. The calibration insert as claimed in claim 1, wherein:
    said solid body is a solid body of organic material of defined transparency.

7. The calibration insert as claimed in claim 1, wherein:
    the calibration insert is so embodied that it can be placed repeatably at the same position at said sensor;
    the calibration insert prevents disturbing light, especially ambient light, from acting on said solid body; and
    the calibration insert protects said solid body from contamination.

8. A calibration insert for adjusting, calibrating and/or checking a function of a nitrate or SAC sensor, which is embodied for measuring at least one measuring variable in a medium, comprising:
    a housing which is essentially transparent for the measuring wavelength and for the reference wavelength; and
    a calibration insert including a solid body, wherein: said solid body is located in said housing; the measuring wavelength and the reference wavelength are different; said housing and said solid body fitting into a gap of said sensor; and
    the transmittance of light of the measuring wavelength and the transmittance of light of the reference wavelength through said slid body are different.

* * * * *